United States Patent [19]

Kasafírek et al.

[11] Patent Number: 4,711,952
[45] Date of Patent: Dec. 8, 1987

[54] SERUM THYMIC FACTOR PEPTIDE ANALOGS AND PROCESS FOR THE PREPARATION THEREOF

[75] Inventors: Evzen Kasafírek; Martin Černý; Petr Kočiš; Jiří Křepelka, all of Prague; Jozef Rovenský, Piestany, all of Czechoslovakia

[73] Assignee: SPOFA, spojene podniky pro zdravotnickouvyrobu, Prague, Czechoslovakia

[21] Appl. No.: 875,230

[22] Filed: Jun. 17, 1986

Related U.S. Application Data

[63] Continuation-in-part of Ser. No. 810,030, Dec. 17, 1985, abandoned.

[30] Foreign Application Priority Data

Dec. 17, 1984 [CS] Czechoslovakia .................. 9887-84

[51] Int. Cl.$^4$ ............................ C07K 7/06; C07K 7/48
[52] U.S. Cl. ................................. 530/327; 530/328; 530/329; 530/330; 530/301
[58] Field of Search ............... 530/327, 328, 329, 330, 530/301

[56] References Cited

U.S. PATENT DOCUMENTS 4,148,886 4/1979 Bach et al. ..................... 530/329
4,301,065 11/1981 Bach et al. ..................... 530/329
4,320,118 3/1982 White et al. .................... 530/328

OTHER PUBLICATIONS

Chemical Abstract 96(19)=163217x, Yanaihara et al. Eur. Pat. Appl. Ep 43247 (1982).
Fok et al., Molecular Immunology, vol. 19, No. 12, pp. 1667–1673, (1982).
Synthesis and Relationship of L–Glutaminyl–L–Histidyl–L–Prolinamide to the Thyrotropin Releasing Hormone.

*Primary Examiner*—John Kight
*Assistant Examiner*—Christina Chan

[57] ABSTRACT

Novel peptide analogs of the serum thymic factor are disclosed, structurally modified, in comparison with the natural substance, both in their N-terminal and C-terminal parts and inside the amino-acid sequence, corresponding to the general formula I A-Gly-Gly-Ser-Asn-B-C-NH-R    (I), in which A is pGlu, Gln, Ala-Lys-Ser-Gln, pGlu-Ala-Lys-Ser-Gln or Gln-Ala-Lys-Ser-Gln, B and C are Gly, Phe, Leu, Ala or a direct bond, and R is H, an alkyl with 1 to 6 carbon atoms or a 2-phenylethyl. Depending upon their chemical structure, the subject thymic factor analogs possess either agonistic (immunostimulative) or antagonistic (immunosuppressory) properties.

10 Claims, No Drawings

SERUM THYMIC FACTOR PEPTIDE ANALOGS AND PROCESS FOR THE PREPARATION THEREOF

This is a cip of Ser. No. 810,030 filed Dec. 17, 1985 now abandoned.

BACKGROUND OF THE INVENTION

The invention relates to serum thymic factor peptide analogs of the general formula I.

$$\text{A-Gly-Gly-Ser-Asn-B-C-NH-R} \qquad (I),$$

in which A is pGlu, Gln, Ala-Lys-Ser-Gln, pGlu-Ala-Lys-Ser-Gln or Gln-Ala-Lys-Ser-Gln, B and C are the same or different and are each Gly, Phe, Leu, Ala or a direct bond, and R is H, an alkyl with 1 to 6 carbon atoms or a 2-phenylethyl group. The invention also relates to a process for the preparation thereof.

Thymic agonists, either the natural hormone isolated from thymus or its synthetic analogs, have recently been adopted in the treatment of immunodeficiency for increasing the patients' immune response, e.g. in systemic diseases lupus erythematodes, myasthenia gravis, infantile asthma, and also in certain neoplastic diseases.

Thymic factor analogs are known. G. Tsukamoto et al., J. Protein Chem. I, 305-15 (1982). The search for such analogs has heretofore focused on the modification of the natural serum thymic factor molecule either inside the amino-acid sequence (pGlu-Ala-Lys-Ser-Gln-Gly$_2$-Ser-Asn) or at its N-terminus (i.e. the left-hand end). Surprisingly, not a single attempt of modification or prolongation at the opposite, C-terminus (the right-hand end) of the sequence has been reported.

SUMMARY OF THE INVENTION

As is evident from the general formula I in comparison with the above structure of the natural substance, the compounds of the present invention, besides optional shortening at the N-terminus, comprise a C-terminal augmentation predominantly by an additional amino-acid residue or residues bearing an amide moiety. Surprisingly, they prove to possess, in dependence on their particular structure, a remarkable immunomodulating activity, either in agonistic (stimulatory) or antagonistic (moderative or even suppressory) sense. Their in-vitro potency, as assessed by the recovery assay of Flymphocytes (Clin. Exp. Immunol. 47, 183, 1982) is comparable to that of natural thymus hormones, e.g. serum thymic factor and purified thymosine fraction V, and in several typical examples it is significantly superior. The respective numerical assay data (positive for immunostimulation and negative for immunosuppression) are summarized in the following table.

TABLE I

| Thymic factor structure or name | Recovery Assay of Flymbocytes differential count % | Please note |
|---|---|---|
| p-Glu—D-Gln—E (natural) | 9.20 | D = Ala—Lys—Ser |
| Thymosine fraction V | 3.80 | |
| D-Gln—E | 3.18 | E = Gly$_2$—Ser—Asn |
| D-Gln—E—GlyNH$_2$ | 12.75 | |
| D-Gln—E—PheNH$_2$ | 16.09 | |
| p-Glu—D-Gln—E—GlyNH$_2$ | 6.31 | |
| p-Glu—D-Gln—E—PheNH$_2$ | 7.54 | |

TABLE I-continued

| Thymic factor structure or name | Recovery Assay of Flymbocytes differential count % | Please note |
|---|---|---|
| Gln—D-Gln—E | −1.64 | |
| Gln—D-Gln—E—PheNH$_2$ | −1.52 | |
| D-Gln—E—PheNHR | −6.0 | R = 2-Ph—ethyl |
| p-Glu—E—GlyNH$_2$ | 6.35 | |
| p-Glu—E—PheNH$_2$ | 2.89 | |
| p-Glu—E—PheNHR | −13.0 | R = 2-Ph—ethyl |
| Gln—E—PheNH$_2$ | −22.9 | |

The previously known structural modifications performed at the N-terminus of the amino-acid sequence of the serum thymic factor indicated the nonsignificance of the pyroglutamyl or glutaminyl residues in position 1, i.e. their presence had only a minor effect on the activity. (Citace G. TSUKAMOTO et al:J. Protein Chem. 1,305 (1982). Contrary to this, in the subject serum thymic factor peptide analogs that comprise an additional C-terminal amino-acid residue terminated with an amide or substituted amide group, the chemical nature of their N-terminal position is critical with regard to both the degree and even for the sense of activity.

The serum thymic factor peptide analogs of the invention can be prepared by common preparative methods generally employed in the synthesis of peptides, e.g. by combining appropriate peptidic fragments (fragment condensation) or by successive step-wise build-up of the desired amino-acid sequence. The process can be conducted either in solution or on a solid carrier, optionally under enzymatic catalysis, and any known protective groups and condensation agents known in the art can be used in principal.

The subject peptide compounds of the general formula I can advantageously be prepared by reacting a peptide compound of the general formula II $$\text{Gly-Gly-Ser-Asn-B-C-NH-R} \qquad (II),$$

in which B, C, and R have the same meanings as in formula I, with a compound of the general formula III $$\text{x-A(Y)} \qquad (III),$$

in which A has the same meaning as in formula I, X and Y are protective groups for protecting alpha or omega amino groups, with the proviso that X and Y can also be H atoms when A is pGlu, to yield a peptide compound of the general formula IV $$\text{X-A(Y)-Gly-Gly-Ser-Asn-B-C-NH-R} \qquad (IV),$$

in which A, B, C, and R have the same meanings as in formula I, and X and Y have the same meanings as in formula III, if required with subsequent successive or simultaneous removal of the protective groups by techniques known per se.

Those of the subject compounds of general formula I in which A stands for a pyroglutamyl residue, and B, C, and R have the aforementioned meaning, can advantageously be obtained by reacting the respective compound of the general formula II with unprotected pyroglutamic acid.

Starting materials required for the preparation are known substances that are available according to known methods described in the relevant literature.

Further particulars of the preparative procedures are illustrated by the following non-limitative examples.

DESCRIPTION OF THE PREFERRED EMBODIMENTS

Explanatory remarks to the experimental part.

Melting temperatures are determined on a Kofler apparatus, and are not corrected. Analytical samples are dried under reduced pressure at 70 kPa over phosphorus pentoxide at room temperature (for compounds melting below 115° C.) or at 105° C. (for compounds melting above 115° C.). Optical rotations are measured at 20° C. and the Na D line wavelength on a Perkin-Elmer 141 polarimeter. The content of water is determined on an Aquatest II Photovolta instrument.

Chromatographic separations are performed on thin layer of silica gel (Kieselgel G, Merck) in the following solvent systems:
$S_1$: 1-butanol-acetic acid-water (4:1:1)
$S_2$: 1-butanol-acetic acid-pyridine-water (15:3:10:6)
$S_3$: 2-propanol-water (2:1)

The detection of free amino acids and peptides is effected with ninhydrin, while the detection of protected peptides is carried out by the standard chlorination technique with the use of 2-tolidine.

Evaporation of solutions is done at reduced pressure on a rotary vacuum evaporator. Unless otherwise stated, the hydrogenations are conducted at atmospheric pressure and ambient temperature. Most of the crystallizations are carried out by the binary solvent technique: the material is dissolved in the first solvent at its boiling temperature, and the other indicated solvent is added to induce crystallization on cooling. Analytical samples are recrystallized, unless otherwise stated, in a manner similar to the preceding solvent system.

The composition of all prepared compounds including new intermediates referred to hereinbelow is verified by elemental analysis, the composition of presumed solvates also by the determination of respective solvent.

EXAMPLE 1

(a) Benzyloxycarbonylasparaginyl-phenylalanine methylester

A solution of benzyloxycarbonylasparagine (13.3 g; 50 mmoles), N-ethylpiperidine (7.0 ml) and pyridine (5.0 ml) in dichloromethane (100 ml) cooled to −20° C. is treated under constant stirring with pivaloylchloride (6.3 ml); the mixture is then stirred and cooled (0° C.) for 8 minutes. After that, within 2 to 3 minutes, a solution of phenylalanine methyl ester, liberated from its hydrochloride (10.7 g; 50 mmoles) by the addition of N-ethylpiperidine (7.0 ml), in dichlormethane (100 ml) is added. The reaction mixture is stirred for an additional 2 hours at room temperature, the precipitated crystalline substance is collected on filter and triturated successively with 1 M hydrochloric acid, water, 5% aqueous sodium hydrogencarbonate solution and water. Crystallization from methanol yields 14.5 g (68%) of the title product, melting at 196°–197° C. An analytical sample is crystallized from dimethylformamide and 2-propanol, and the m.p. remains unchanged. Chromatography: $R_f$ 0.71/$S_1$, 0.75/$S_2$. Optical rotation $[\alpha]_D^{20}$ −2.0° (c 0.2; dimethylformamide). The elemental composition corresponds to the summary formula $C_{22}H_{25}N_3O_6$.

(b) Asparaginyl-phenylalanine methyl ester hydrobromide

The preceding methyl ester (4.3; 10 mmoles) dissolved in glacial acetic acid (7.0 ml) is treated with a 38% hydrogen bromide solution in acetic acid (10 ml), and the mixture is allowed to stand at room temperature for 1 hour. The product is precipitated by the addition of ether, separated, washed with ether and dried in a desiccator over sodium hydroxide and phophorus pentoxide to give 3.6 g (97%) of the title substance, homogenous electrophoretically and chromatographically. $R_f$ 0.37/$S_1$, 0.70/$S_2$.

(c) Benzyloxycarbonylseryl-asparaginyl-phenylalanine methyl ester

Benzyloxycarbonylserine (8.4 g; 35 mmoles), N-ethylpiperidine (4.9 ml) and pyridine (3.5 ml) in dichlormethane (100 ml) cooled to −20° C. are treated under constant stirring with pivaloylchloride (4.4 ml); the mixture is stirred and cooled (0° C.) a further 8 minutes. After that, within 2 to 3 minutes, a solution of asparaginyl-phenylalanine methyl ester, liberated from its hydrobromide (13.1 g; 35 mmoles) by the addition of N-ethylpiperidine (4.9 ml), in dichloromethane (100 ml) is added. The reaction mixture is stirred for 2 hours at room temperature and evaporated. The noncrystalline residue is dissolved in ethyl acetate and the solution is successively washed with 1 M hydrochloric acid, water, 5% sodium hydrogencarbonate and water, dried over anhydrous sodium sulfate, and evaporated, after which the residue is crystallized from methanol. The yield is 9.1 g (51%), m.p. 180°-183° C. A sample is recrystallized from the same solvent and has m.p. 184°-186° C. $R_f$ 0.71/$S_1$, 0.82/$S_2$. $[\alpha]_D^{20}$ −13.8° (c 0.2; methanol). Composition: $C_{25}H_{30}N_4O_8$.

(d) Benzyloxycarbonylseryl-asparaginyl-phenylalanine amide

A precooled solution of the preceding ester (5.2 g; 10 mmoles) in 98% methanol (130 ml) is treated with liquid ammonia (approx. 33 g), and the reaction mixture is allowed to stand at room temperature for 70 hours. The precipitated crystalline product is separated and washed with methanol to yield 3.9 g (78%) of the product melting at 218°-221° C. A sample is crystallized from dimethylformamide-methanol (1:1) by the addition of ether and has m.p. 222°-224° C. A sample is crystallized from dimethylformamide-methanol (1:1) by the addition of ether and has m.p. 222°-224° C. $R_f$ 0.64/$S_1$, 0.71/$S_2$.$[\alpha]_D^{20}$ −15.9° (c 0.2; dimethylformamide). Composition: $C_{24}H_{29}N_5O_7$.

(e) Seryl-asparaginyl-phenylalanine amide

A solution of the preceding amide (5.0 g; 10 mmoles) and acetic acid (0.1 ml) in 70% methanol (400 ml) is admixed with Pd black (approx. 50 mg) and hydrogenated for 3 hours. After removing of the catalyst, the solution is evaporated and the solid residue is crystallized from 95% methanol-ether to give 3.6 g (96%) of the product, m.p. 169°-172° C. A sample is recrystallized, the m.p. remains unchanged. $R_f$ 0.24/$S_1$, 0.57/$S_2$.$[\alpha]_D^{20}$ −19.3° (c 0.2; methanol). Composition: $C_{16}H_{23}N_5O_5 \cdot \frac{1}{2}H_2O$.

(f) Benzyloxycarbonylglutaminyl-glycyl-glycine methyl ester

A suspension of glycyl-glycine methyl ester hydrochloride (1.9 g; 10 mmoles) in a dimethylformamide-dichloromethane (1:2) mixture (30 ml) is admixed with N-ethylpiperidine (1.4 ml) and stirred for 2 hours at room temperature. After that benzyloxycarbonylglutamine pentachlorphenyl ester (5.3 g; 10 mmoles) is added and the reaction mixture is stirred at room temperature a further 4 hours. After 8 hours of standing, the precipitated crystalline product is separated and crystallized from methanol - dichloromethane. Yield 2.5 g (61%), m.p. 129°-134° C., after additional crystallization from methanol 132°-134° C. $R_f 0.57/S_1$, $0.78/S_2.[\alpha]_D^{20} -8.5°$ (c 0.2; 50% acetic acid). Composition: $C_{18}H_{24}N_4O_7.\frac{1}{2}H_2O$.

(g) Benzyloxycarbonylglutaminyl-glycyl-glycine hydrazide

To the preceding ester (8.3 g; 20 mmoles) dissolved in methanol (100 ml) there are added 100% hydrazine hydrate (4.7 ml). After 48 hours of standing at room temperature, the crystalline phase is separated, washed with methanol and crystallized from 80% ethanol to yield 6.1 g (74%) of the product melting at 169°-171° C. $R_f 0.30/S_1$, $0.70/S_2.[\alpha_D^{20} -9.1°$ (c 0.2; methanol). Composition: $C_{17}H_{24}N_6O_6$.

(h) Benzyloxycarbonylglutaminyl-glycyl-glycyl-seryl-asparaginyl-phenylalanine amide A solution of the preceding hydrazide (4.1 g; 10 mmoles) and concentrated hydrochloric acid (4.0 ml) in dimethylformamide (50 ml) cooled to −20° C. is admixed with 3.6 M sodium nitrite solution (2.8 ml). The reaction mixture is stirred and cooled (−20° C.) for 10 minutes, then adjusted by the addition of N-ethylpiperidine to pH 6.9, and a solution of seryl-asparaginyl-phenylalanine amide (3.7 g; 10 mmoles) in dimethylformamide (50 ml) is added. After 12 hours of standing at 0° C., the solution is evaporated and the solid residue is triturated successively with 1 M hydrochloric acid, water, 5% sodium hydrogencarbonate solution and water and crystallized from 1-butanol-ethyl acetate. Yield 5.6 g (74%), m.p. 225°-227° C.

A sample is recrystallized similarly and has m.p. 226°-229° C. $R_f 0.30/S_1$, $0.58/S_2.[\alpha]_D^{20} -12.1°$ (c 0.2; dimethylformamide). Amino-acid analysis: Glu 1.00, Gly 2.02, Ser 0.76, Asp 0.94, Phe 0.92. Composition: $C_{33}H_{43}N_9O_{11}. H_2O$.

(i) Glutaminyl-glycyl-glycyl-seryl-asparaginyl-phenylalanine amide

The preceding amide (2.2 g; 3 mmoles) is hydrogenated in dimethylformamide - methanol (1:2; 100 ml) acidified with acetic acid (0.1 ml) over Pd black (approx. 25 mg) for 6 hours. after separation of the catalyst, the filtrate is evaporated and the solid residue is crystallized from 95% methanol by the addition of ether. Yield 1.7 g (86%), m.p. 202°-204° C., after recrystallization 209°-212° C. $R_f$ $0.05/S_1$, $0.42/S_2.[\alpha]_D^{20} -21.9°$ (c 0.2; 50% methanol). Composition: $C_{25}H_{37}N_9O_9. 3H_2O$.

EXAMPLE 2

(a) Alanyl-Nω-benzyloxycarbonyllysyl-serine methyl ester hydrochloride

A solution of tert-butyloxycarbonylalanyl-Nω-benzyloxycarbonyllysyl-serine methyl ester (3.4 g; 6 mmoles) in glacial acetic acid (12 ml) is treated with 1 M hydrogen chloride solution in the same solvent (12 ml). The reaction mixture is allowed to stand at room temperature for 1 hour and the product is precipitated with ether, separated and dried in a desiccator over sodium hydroxide and phosphorus pentoxide to yield 2.7 g (93%) of the title compound with $R_f 0.35/S_1$, $0.62/S_2$.

(b) Pyroglutamyl-alanyl-Nω-benzyloxycarbonyllysylserine methyl ester

A solution of pyroglutamic acid (0.9 g; 7 mmoles), N-hydroxybenztriazole (0.95 g) and N, N'-dicyclohexylcarbodiimide (1.6 g) in dimethylformamide (50 ml) is stirred and cooled (−10° C.) for 10 minutes. The reaction mixture is treated with precooled (−10° C.) solution of alanyl-N-benzyloxycarbonyllysyl-serine methyl ester, liberated from the preceding hydrochloride (3.4 g; 7 mmoles) by the addition of N-ethylpiperidine (1.0 ml), in dimethylformamide (50 ml). The reaction mixture is stirred for 2 hours at 0° C. and then allowed to stand for 8 hours at room temperature. The N,N'-dicyclohexylurea precipitate is filtered off, the filtrate is evaporated, the noncrystalline residue is dissolved in ethyl acetate, washed successively with 1% aqueous citric acid, water, 5% sodium hydrogencarbonate and water, dried over anhydrous sodium sulfate, evaporated and crystallized from 2-propanol. The yield is 2.4 g (59%), m.p. 120°-122° C. After recrystallization, the product melts at 135°-137° C. and has $R_f$ $0.53/S_1$, $0.83/S_2.[\alpha]_D^{20} -24.4°$ (c 0.2; dimethylformamide). Amino-acid analysis: Glu 0.85, Lys 1.00, Ala 1.06, Ser 0.82. Composition: $C_{26}H_{37}N_5O_9. H_2O$.

(c) Pyroglutamyl-alanyl-Nω-benzyloxycarbonyllysylserine hydrazide

The preceding ester (2.9 g; 5 mmoles) is dissolved in dimethylformamide-methanol (1:1; 40 ml) and 100% hydrazine hydrate (3.0 ml) is added. After 8 hours of standing at room temperature, the precipitated crystalline product is collected on filter and washed with methanol. The yield is 2.3 g (79%), m.p. 212°-214° C., after recrystallization from 80% methanol 217°-218° C. $R_f$ $0.54/S_1$, $0.73/S_2.[\alpha]_D^{20} -48.9°$ (c 0.2; 80% methanol). Composition: $C_{25}H_{37}N_7O_8. H_2O$.

(d) Pyroglutamyl-alanyl-Nω-benzyloxycarbonyllysylseryl-glutaminyl-glycyl-glycyl-seryl-asparaginyl-phenylalanine amide A solution of the preceding hydrazide (0.95 g; 1.63 mmoles) and concentrated hydrochloric acid (0.6 ml) in dimethylformamide (20 ml) precooled to −20° C. is admixed with a 3.6 M sodium nitrite solution (0.5 ml). After adjusting the mixture by the addition of N-ethylpiperidine to pH 6.9, a solution of glutaminyl-glycyl-glycyl-seryl-asparaginyl-phenylalanine amide (0.92 g; 1.51 mmole) in dimethylformamide (40 ml) is added. After 12 hours of standing at 0° C., the reaction mixture is evaporated and the noncrystalline residue is mixed with a saturated sodium chloride solution (2.0 ml); after standing for another hour at the same temperature, the crystalline product is separated, washed and crystallized from butanol saturated with water at 20° C. by the addition of ethyl acetate and recrystallized from 80% aqueous methanol-ethyl acetate. Yield 0.58 g (33%), m.p. 248°–252° C., after recrystallization 259°–261° C. $R_f 0.08/S_1$, $0.42/S_2$.$[\alpha]_D^{20} -48.2°$ (c 0.1; 50% aqueous acetic acid). Amino-acid analysis: Glu 1.90, Ala 1.18, Lys 1.06, Ser 1.79, Gly 1.95, Asp 1.05, Phe 1.00. Composition: $C_{50}H_{70}N_{14}O_{17}$. $2H_2O$.

(e)

Pyroglutamyl-alanyl-lysyl-seryl-glutaminyl-glycyl-glycyl-seryl-asparaginyl-phenylalanine amide The preceding amide (300 mg; 0.26 mmole) is hydrogenated over Pd black (approx. 20 mg) in 10% aqueous acetic acid (100 ml) at atmospheric pressure and room temperature for 3 hours. After separation of the catalyst, the solution is evaporated, the residue is dissolved in 0.2 M acetic acid (5.0 ml) and purified by gel filtration on Sephadex G 15 (column size 1.8×90 cm); homogeneous fractions are concentrated and freeze-dried to give 200 mg (64%) of the chromatographically uniform product. $R_f 0.02/S_1$, $0.25/S_2$.$[\alpha]_D^{20} -67.9°$ (c 0.1; 0.1 M acetic acid). Amino-acid analysis: Glu 1.94, Ala 1.18, Lys 1.10, Ser 1.78, Gly 2.03, Asp 1.04, Phe 1.00. Composition: $C_{42}H_{64}N_{17}O_{13}$ 2 AcOH. 4 $H_2O$.

EXAMPLE 2A

Pyroglutamyl-glycyl-glycyl-seryl-asparaginyl-phenylalanine amide

Benzyloxycarbonylglutaminyl-glycyl-glycyl-seryl-asparaginyl-phenylalanine amide (4.0 g; 5.26 mmoles) in 10% acetic acid (100 ml) is hydrogenated over Pd black (approx. 25 mg) at 40° C. under atmospheric pressure for 3 hours. After filtering off the catalyst, the solution is evaporated, the remaining crude product is dissolved in 0.2 M acetic acid (5 ml) and purified by gel filtration on Sephadex G 15; homogeneous fractions are combined, concentrated and freeze-dried. The yield is 2.5 g (77%), m.p. 218°–221° C. $[\alpha]_D^{20} -35.7°$ (c 0.1, 1 M acetic acid). The substance is chromatographically uniform (ninhydrin test is negative). $R_f$ $0.15/S_1$, $0.56/S_2$.[Amino-acid analysis: Glu 1.00, Gly 2.00, Ser 0.87, Asp 1.04, Phe 0.97. Composition: $C_{24}H_{33}N_8O_9$.

EXAMPLE 3

(a)

tert-Butyloxycarbonylalanyl-Nω-benzyloxycarbonyllysyl-serine

A solution of tert-butyloxycarbonylalanyl-Nω-benzyloxycarbonyllysyl-serine methyl ester (2.0 g, 3.6 mmoles) in methanol (20 ml) is made alkaline with 1 M sodium hydroxide solution (5.4 ml), then stirred for 30 minutes at room temperature, neutralized to pH 7.0. The solvent is distilled off, the aqueous residue is adjusted with 1 M hydrochloric acid to pH 3, and the liberated product is taken into ethyl acetate (3×100 ml). Combined organic extracts are dried over anhydrous sodium sulfate, evaporated, and the residue is crystallized from ethyl acetate - petroleum ether. The yield is 1.7 g (88%) of the product, melting at 132°–134° C. After recrystallization from the same solvent system, the m.p. remains unchanged. $R_f$ $0.75/S_1$, $0.75/S_2$.$[\alpha]_D^{20} -23.2°$ (c 0.2, methanol). Composition: $C_{25}H_{38}N_4O_9$.

(b)

tert-Butyloxycarbonylalanyl-Nω-benzyloxycarbonyllysyl-seryl-glutaminyl-glycyl-glycyl-seryl-asparaginyl-phenylalanine amide A solution of the preceding serine derivative (0.8 g, 1.49 mmole), N-hydroxybenzotriazole (0.2 g) and N, N'-dicyclohexylcarbodiimide (0.3 g) in dimethylformamide (30 ml) is stirred and cooled at −10° C. for 10 minutes. A precooled (−10° C.) solution of glutaminyl-glycyl-glycyl-seryl-asparaginyl-phenylalanine amide (1.0 g, 1.51 mmole) in the same solvent (50 ml) is added. The reaction mixture is stirred for 2 hours at 0° C. and then allowed to stand for 8 hours at room temperature. After filtering off the formed N, N'-dicyclohexylurea, the solution is evaporated and the noncrystalline residue is mixed with saturated brine (sodium chloride solution, 3.0 ml). After 1 hour of standing at 0° C., the crystalline product is separated, washed and crystallized from 1-butanol saturated with water at 20° C. by the addition of ethyl acetate to give 0.4 g (23%) of the substance, melting at 225°–227° C. A sample is recrystallized and the m.p. is unchanged. $R_f 0.25/S_1$, $0.76/S_2$.$[\alpha]_D^{20} -39.2°$ (c 0.1, 50% acetic acid). Amino-acid analysis: Ala 1.03, Lys 0.98, Ser 1.77, Glu 0.94, Gly 2.03, Asp 1.00, Phe 1.03. Composition: $C_{50}H_{73}N_{13}O_{17}$. $H_2O$.

(c)

Alanyl-lysyl-seryl-glutaminyl-glycyl-glycyl-seryl-asparaginyl-phenylalanine amide The preceding peptide derivative (0.4 g, 0.35 mmole) is deprotected by hydrogenation over Pd black (approx. 20 mg) in 10% acetic acid (100 ml) at atmospherical pressure and room temperature for 2 hours. After removal of the catalyst, the solution is evaporated, the residue is dried in a desiccator over sodium hydroxide and phosphorus pentoxide for 5 hours and dissolved in trifluoroacetic acid (1.8 ml). The solution is stirred for 1 hour at room temperature, the product is precipitated with ether, separated, washed, dried as above for 2 hours and dissolved in 50% methanol. A conversion on Zerolite FF anion exchanger in the acetate cycle (first batchwise, then on a column 1.8×25 cm) yields the corresponding acetate. Combined methanolic eluates are evaporated, the residue is dissolved in 0.2. M acetic acid and purified by gel filtration on Sephadex G 15 as described in Example 1. The yield is 0.2 g (57%) of a uniform product. $R_f 0.02/S_1$, $0.45/S_2$.$[\alpha]_D^{20} -40.4°$ (c 0.1, 0.1 M acetic acid). Amino-acid analysis: Ala 1.09, Lys 1.03, Ser 1.65, Glu 1.00, Gly 1.97, Asp 1.02, Phe 0.98. Composition: $C_{37}H_{59}N_{13}O_{13}$. 2 AcOH.

EXAMPLE 4

(a)

Alanyl-Nω-benzyloxycarbonyllysyl-seryl-glutaminyl-glycyl-glycyl-seryl-asparaginyl-phenylalanine amide trifluoroacetate A solution of the corresponding tert-butyloxycarbonylalanyl peptide amide (1.0 g, 0.87 mmole) and anisole (0.3 ml) in trifluoroacetic acid (2.7 ml) is stirred for 30 minutes at room temperature. The product is precipitated by the addition of ether, separated, washed and dried over sodium hydroxide and phosphorus pentoxide to give 0.9 g (89%) of the substance having $R_f 0.21/S_1$, $0.65/S_2$.

(b)
Benzyloxycarbonylglutaminyl-alanyl-Nω-benzyloxycarbonyllysyl-seryl-glutaminyl-glycyl-glycyl-seryl-asparaginyl-phenylalanine amide.

Benzyloxycarbonylglutamine (250 mg, 0.89 mmole), N-hydroxybenzotriazole (120 mg) and N, N'-dicyclohexylcarbodiimide (200 mg) dissolved in dimethylformamide (30 ml) are stirred and cooled (−10° C.) for 10 minutes. A precooled solution (−10° C.) of the preceding amide liberated from its trifluoroacetate (995 mg; 0.87 mmole) by the addition of 0.15 ml of N-ethypiperidine in dimethylformamide (30 ml) is added. The reaction mixture is stirred for 2 hours at 0° C. and then allowed to stand for 8 hours at room temperature. After evaporation to approx. a half of the initial volume, and subsequent cooling (1 hour at 0° C.), the N, N'-dicyclohexylurea precipitate is filtered off and the filtrate is evaporated to dryness. The solid residue is mixed with water (3 ml) and the crystalline product is separated and crystallized from acetic acid-ethyl acetate to give 200 mg (18%) of the substance, melting at 251°–254° C. (unchanged after recrystallization). $R_f$ 0.02/$S_1$, 0.03/$S_2$.$[\alpha]_D^{20}$ −38.8° (c 0.1, 25% acetic acid). Amino-acid analysis: Glu 1.84, Ala 0.95, Lys 1.11, Ser 1.73, Gly 2.04, Asp 1.00, Phe 1.09. Composition: $C_{58}H_{79}N_{15}O_{19} \cdot 2H_2O$.

(c)
Glutaminyl-alanyl-lysyl-seryl-glutaminyl-glycyl-glycyl-seryl-asparaginyl-phenylalanine alanine amide The preceding benzyloxycarbonylglutaminyl peptide amide (100 mg, 0.08 mmole) is hydrogenated in 10% acetic acid (100 ml) acidified with 1 M hydrochloric acid (0.4 ml) over Pd black (approx. 30 mg) at atmospheric pressure and room temperature for 3 hours. After removal of the catalyst and evaporation of the filtrate, the residue is dissolved in water (5 ml) and again evaporated; this is repeated twice. The solid residue is dissolved in 0.2 M acetic acid and purified by gel filtration on Sephadex G 15 as described in Example 1. Yield 70 mg (75%). $R_f$0.00/$S_1$, 0.25/$S_2$.$[\alpha]_D^{20}$ −47.8° (c 0.1 M acetic acid). Amino-acid analysis Glu 1.92, Ala 1.00, Lys 0.99, Ser 1.77, Gly 2.04, Asp 1.01, Phe 0.97. Composition: $C_{42}H_{67}N_{15}O_{15} \cdot 2HCl \cdot 4H_2O$.

EXAMPLE 5

(a) Benzyloxycarbonylasparaginyl-phenylalanine 2-phenylethylamide is prepared by the mixed-anhydride technique similar to the preparation of the corresponding methyl ester in example 1. Yield 70%, m.p. 239°–243° C. (acetic acid-ether). Composition: $C_{29}H_{32}N_4O_5 \cdot 0.5 AcOH$.

The product is de-protected by the common technique employing hydrogen bromide solution in acetic acid. After one hour of standing at room temperature, the hydrobromide is precipitated by the addition of ether, separated, thoroughly washed with the same solvent and dried for 12 hours over sodium hydroxide and phosphorus pentoxide to yield asparaginyl-phenylalanine 2-phenylethylamide hydrobromide, $R_f$ 0.48/$S_1$, 0.53/$S_2$.

(b) Benzyloxycarbonylglycyl-glycyl-serine hydrazide

A solution of benzyloxycarbonylglycyl-glycine (13.31 g, 50 mmoles), N-hydroxysuccinimide (5.75 g) and N, N'-dicyclohexylcarbodiimide (11.3 g) in dimethylformamide (180 ml) is stirred and cooled (−10° C.) for 1 hour. A precooled (−10° C.) solution of serine methyl ester, liberated from its hydrochloride (7.8 g, 50 mmoles) with N-ethylpiperidine (6.85 ml), in the same solvent (50 ml) is added, and the reaction mixture is stirred for 3 hours at 0° C. and allowed to stand for 8 hours at room temperature; the N, N'-dicyclohexylurea precipitate is filtered off and the filtrate is admixed with 100% hydrazine hydrate (15 ml). After 3 days of standing at room temperature, the formed hydrazide is separated, washed with ethanol and crystallized from aqueous ethanol. Yield 15.2 g (83%), m.p. 172-175 (unchanged after recrystallization). Composition: $C_{15}H_{21}N_5O_6$.

(c)
Benzyloxycarbonylglycyl-glycyl-seryl-asparaginyl-phenylalanine 2-phenylethylamide A solution of the preceding hydrazide (3.7 g, 10 mmoles) and concentrated hydrochloric acid (4 ml) in dimethylformamide (80 ml) is precooled to −30° C. and treated with a solution of sodium nitrite (690 mg) in water (2.8 ml). After 10 minutes of stirring at −25° C., the mixture is adjusted with N-ethylpiperidine to pH 6.9 and added to a precooled (−30° C.) solution of asparaginylphenylalanine 2-phenylethyl amide, liberated from the preceding hydrobromide (10 mmoles) with approx. 1.6 ml of N-ethylpiperidine, in dimethylformamide (50 ml). After standing at 3° C. the reaction mixture is evaporated, the product is precipitated by the addition of water, separated, triturated successively with 1 M hydrochloric acid, water, 5% sodium hydrogencarbonate and water, and crystallized from acetic acid-ether. The yield is 2.45 g (43%), m.p. 225°–229° C.

(d)
Glycyl-seryl-asparaginyl-phenylalanine 2-phenylamide is obtained by de-protecting of the previous benzyloxycarbonyl derivative with hydrogen bromide in acetic acid to give the hydrobromide, m.p. 227°–230° C., $R_f$ 0.52/$S_1$, 0.71/$S_2$, composition: $C_{28}H_{37}N_7O_7 \cdot 2 HBr \cdot 0.5 AcOH$. The title base is liberated from the hydrobromide with 10% aqueous ammonia in dimethylformamide, isolated by dilution with water and crystallized from dimethylformamide - ether. Yield 51%, m.p. 223°–226° C. $R_f$0.61/$S_1$, 0.74/$S_2$.

EXAMPLE 6

Pyroglutamyl-glycyl-glycyl-seryl-asparaginyl-phenylalanine 2-phenylethylamide is prepared from pyroglutamic acid and glycyl-glycyl-seryl-asparaginyl-phenylalanine 2-phenylethylamide using the carbodiimide method similar to that described in the preceding example 5. Yield 82 %, m.p. 209°–211° C., $R_f$0.25/$S_1$, 0.67/$S_2$.

EXAMPLE 7

(a)

Benzyloxycarbonylseryl-asparaginyl-glycine 4, 4'-dimethoxybenzhydrylamide is obtained from benzyloxycarbonylseryl-asparagine hydrazide and glycine 4, 4'-dimethoxybenzhydrylamide by the procedure described in Example 1. Yield 64%, m.p. 160°–162° C. (dimethylformamide-methanol-ether), $R_f$ 0.68/$S_1$, 0.80/$S_2$.

(b)

N$^{alpha}$-Benzyloxycarbonylglutaminyl-glycyl-glycyl-seryl-asparaginyl-glycine 4, 4'-dimethoxybenzhydrylamide, similarly from N$^{alpha}$-benzyloxycarbonylglutaminyl-glycyl-glycine hydrazide and seryl-asparaginyl-glycine 4, 4'-dimethoxybenzhydrylamide, yield 54%, m.p. 200°–202° C. (dimethylformamide - ethyl acetate), R$_f$ 0.38/S$_1$, 0.85/S$_2$, composition: C$_{41}$H$_{51}$N$_9$O$_{13}$. H$_2$O.

(c)

Pyroglutamyl-glycyl-glycyl-seryl-asparaginyl-glycine amide is prepared by catalytic hydrogenation of the preceding compound in 10% acetic acid acidified with hydrochloric acid as described in Example 1 and subsequent de-protection of the 4, 4'-dimethyloxybenzhydrylamide base (R$_f$ 0.10/S$_1$, 0.63/S$_2$, 0.36/S$_3$ with trifluoroacetic acid in boiling anisole. Yield 66% (benzhydrylamide cleavage step), R$_f$ 0.01/S$_1$, 0.03/S$_2$, $[\alpha]_D^{20}$ −27.5° (c 0.1, 0.1 M acetic acid).

With use of analogous preparative procedures, the following peptide compounds of the invention are also prepared:

Glutaminyl-glycyl-glycyl-seryl-asparaginyl-phenylalanine 2-phenylethylamide, R$_f$ 0.18/S$_1$, 0.51/S$_2$.

Glutaminyl-glycyl-glycyl-seryl-asparaginyl-phenylalanyl-phenylalanine amide, R$_f$ 0.08/S$_1$, 0.31/S$_2$.

Pyroglutamyl-glycyl-glycyl-seryl-asparaginyl-phenylalanyl-phenylalanine amide, m.p. 250°–253° C. (dimethylformamide-ether), R$_f$ 0.22/S$_1$, 0.51/S$_2$.

Glutaminyl-glycyl-glycyl-seryl-asparaginyl-alanine amide, R$_f$ 0.00/S$_1$, 0.11/S$_2$.

Glutaminyl-glycyl-glycyl-seryl-asparaginyl-alanyl-alanine amide, m.p. 181°–185° C. (decomp.), R$_f$ 0.00/S$_1$, 0.04/S$_2$.

Alanyl-lysyl-seryl-glutaminyl-glycyl-glycyl-seryl-asparaginyl-alanine amide hydrogen-trifluoroacetate, m.p. 178°–181° C. (decomp.), R$_f$ 0.00/S$_1$, 0.02/S$_2$.

Alanyl-lysyl-seryl-glutaminyl-glycyl-glycyl-seryl-asparaginyl-glycine amide, R$_f$ 0.01/S$_1$, 0.18/S$_2$.

We claim:

1. Serum thymic factor peptide analog of the general formula I

A-Gly-Gly-Ser-Asn-B-C-NH-R    (I), in which A is pGlu, Gln, Ala-Lys-Ser-Gln, pGlu-Ala-Lys-Ser-Gln or Gln-Ala-Lys-Ser-Gln; B and C are the same or different and are each Gly, Phe, Leu, Ala or a direct bond, and R is H, an alkyl with 1 to 6 carbon atoms or a 2-phenylethyl group.

2. The analog of claim 1, which is alanyl-lysyl-seryl-glutaminyl-glycyl-glycyl-seryl-asparaginyl-glycine amide.

3. The analog of claim 1, which is alanyl-lysyl-seryl-glutaminyl-glycyl-glycyl-seryl-asparaginyl-phenylalanine amide.

4. The analog of claim 1, which is pyroglutamyl-alanyl-lysyl-seryl-glutaminyl-glycyl-glycyl-seryl-asparaginyl-glycine amide.

5. The analog of claim 1, which is pyroglutamyl-alanyl-lysyl-seryl-glutaminyl-glycyl-glycyl-seryl-asparaginyl-phenylalanine amide.

6. The analog of claim 1, which is pyroglutamyl-glycyl-glycyl-seryl-asparaginyl-glycine amide.

7. The analog of claim 1, which is pyroglutamyl-glycyl-glycyl-seryl-asparaginyl-phenylalanine amide.

8. The analog of claim 1, which is alanyl-lysyl-seryl-glutaminyl-glycyl-glycyl-seryl-asparaginyl-phenylalanine 2-phenylethylamide.

9. The analog of claim 1, which is pyroglutamyl-glycyl-glycyl-seryl-asparaginyl-phenylalanine 2-phenylethylamide.

10. The analog of claim 1, which is glutaminyl-glycyl-glycyl-seryl-asparaginyl-phenylalanine amide.

* * * * *